(12) United States Patent
Van Stone

(10) Patent No.: US 9,364,369 B2
(45) Date of Patent: Jun. 14, 2016

(54) HEAD AND NECK SUPPORT APPARATUS

(71) Applicant: Melinda Van Stone, Palmdale, CA (US)

(72) Inventor: Melinda Van Stone, Palmdale, CA (US)

(*) Notice: Subject to any disclaimer, the term of this patent is extended or adjusted under 35 U.S.C. 154(b) by 197 days.

(21) Appl. No.: 14/280,509

(22) Filed: May 16, 2014

(65) Prior Publication Data

US 2015/0328039 A1 Nov. 19, 2015

(51) Int. Cl.
*A61B 19/00* (2006.01)
*A61F 5/37* (2006.01)

(52) U.S. Cl.
CPC ............. *A61F 5/3707* (2013.01); *A61F 5/3776* (2013.01); *A61F 5/3792* (2013.01)

(58) Field of Classification Search
CPC ... A61F 5/3707; A61F 5/3769; A61F 5/3776; A61F 5/3796; A42B 1/24; A42B 3/0473
USPC ........................................ 128/869; 2/6.2, 171
See application file for complete search history.

(56) References Cited

U.S. PATENT DOCUMENTS

| | | | | |
|---|---|---|---|---|
| 2,638,293 A * | 5/1953 | Lindstrom | ............ | A42B 3/0473 244/122 AE |
| 4,707,031 A * | 11/1987 | Meistrell | ............... | B60R 22/001 128/869 |
| 5,988,173 A * | 11/1999 | Scruggs | ................. | A61F 5/3707 128/870 |
| 6,301,716 B1 * | 10/2001 | Ross | ...................... | A61F 5/3707 2/171 |
| 6,607,245 B1 * | 8/2003 | Scher | ...................... | A47C 7/383 297/393 |
| 7,032,597 B1 * | 4/2006 | Frank | ........................ | A61F 5/56 128/846 |
| 8,287,045 B1 * | 10/2012 | Donohue | ............. | B60N 2/2812 297/391 |
| 8,381,316 B2 * | 2/2013 | Edwards | ................. | A42B 1/006 2/175.3 |
| 9,089,179 B2 * | 7/2015 | Tagg | ......................... | A42B 1/24 |
| 2006/0061186 A1 * | 3/2006 | Funke, III | ............... | A47C 7/383 297/393 |
| 2007/0083987 A1 * | 4/2007 | Mothaffar | ............ | A42B 3/0473 2/468 |

* cited by examiner

*Primary Examiner* — Kristen Matter

(74) *Attorney, Agent, or Firm* — Omni Legal Group; Omid E. Khalifeh

(57) ABSTRACT

In accordance with one embodiment, a head and neck support apparatus is provided that comprises a seat attachment portion and a portion which is worn by the child passenger. The worn portion comprises an elastic member that will, when worn, encircle the child's head. The rear of the worn portion will further comprise a first engagement member which will removably connect to a second engagement member connected to the seat where the child may foreseeably fall asleep.

7 Claims, 5 Drawing Sheets

HEAD AND NECK SUPPORT APPARATUS

CROSS-REFERENCE TO RELATED APPLICATIONS

None.

NOTICE OF COPYRIGHT AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure as it appears in the Patent and Trademark Office patent files or records, but otherwise reserves all copyright and trade dress rights whatsoever.

TECHNICAL FIELD

The present invention relates to the field of child car seats, strollers, booster seats, and the like; and more particularly to a child head support system for the same.

DISCUSSION OF THE RELATED ART

Proper head and neck support is extremely important for human beings, and particularly so for young children and infants. Often, the motions experienced while riding in a vehicle or in a stroller promote the desire to fall asleep and fall forward or to the side placing the head and neck in dangerous and potentially harmful positions.

Once they have fallen asleep, the head of an infant or toddler is prone to swaying while the child is in motion while in their stroller, carseat, vehicle adult seat, wheelchair, or the like. This is because the muscles in the neck and back, which normally support the head, become relaxed or are too weak to support the child's head. Moreover, in the case of infants and small children, these muscles are not strong enough to hold the child's head in a particular position. As a result, they are prone to dropping the head when any external force acts on them.

In other children, and adults, a medical condition may have caused these muscles to deteriorate thus rendering them incapable of supporting the head while allowing proper spinal alignment and oxygenation brain. As a result, the head is pulled into awkward and potentially dangerous positions such as when it tilts to the left or right, or falls forward. The forces exerted on the child delicate body are similar to those experienced by babies with shaken baby syndrome. These positions strain the neck and spine making them vulnerable to a myriad of dangers particularly those related to the child's delicate nervous system.

In the context of the child carseat, these risks are magnified. Forces resulting from vehicle acceleration, braking, and vehicle cornering, can increase the risk of injury to an unsupported neck. Accordingly, a variety of neck support systems have been proposed in the art with the hopes of addressing this problem and mitigating the risk of injury for the child. However, the prior art lacks the salient features and advantages of the present invention as described herein. The following is a summary of some attempts at addressing this common problem.

U.S. Pat. No. 2,726,714 to McAndrews discloses an infant restraining means for automobile use. The '714 patent comprises a strap which fits around the back of an automobile seat and a belt mounted on the strap, the belt being adjustable to fit around the abdomen of an infant. The '714 patent does not teach an apparatus that is used with a modern forward-facing child car seat or that can be used as a retrofit on a stroller, carseat, highchair, or any place where a seated child fall asleep.

U.S. Pat. No. 3,606,885 to Lund discloses an infant holder of a preformed unitary plastic body by which an infant can be supported either in a relatively fixed supine position or in a suspended upright position for the making of an X-ray or other treatment or operation, and which not only will not interfere with the X-ray but will stand sterilization. The '885 patent does not disclose an apparatus that can be used with a modern car seat during vehicle operation. Furthermore, the '885 patent does not comprise a means of dissipating the forces that would otherwise hurt the child in the event of a sudden impact.

U.S. Pat. No. 4,607,885 to del Fierro discloses a head-restraining device for preventing possibly injurious forward and lateral motion of the head of a child seated in a child's seat. The device comprises a rigid U-shaped restraining member which surrounds the forward and lateral portions of the child's head, and is of a size to be separated therefrom by a slight air gap so as to not be uncomfortable, yet be capable of being engaged by the child's head and restraining such from any more than minimal forward and lateral motion. The device disclosed by the '85 is rigid and lacks the elasticity necessary to ensure a comfortable fit for the child wearing the device. In an addition to the discomfort of wearing the device, a child restrained in such a manner may be exposed to more dangerous forces in a collision resulting from the way in which the device immobilizes the child's head.

U.S. Pat. No. 4,707,031 to Meistrell discloses a head support for a traveler sitting in a chair having a headrest, and which includes a first band adapted to be fitted in adjustably wrapped condition closely about the user's head and at eye or forehead level, a band retention structure associated with the band for retaining the band in said wrapped condition, and a head restraint structure coupled to the band and adapted to be coupled to the headrest for restraining the user's head against lateral side-to-side movement relative to the headrest. Installation of the '031 requires several steps, and the apparatus contains several parts. In addition, the '031 patent does not allow for adjustments to accommodate various size heads.

U.S. Pat. No. 5,076,264 to Lonardo et al. discloses a medical appliance, having a thick foam core received within a cover made of fleece, for simultaneously treating spinal, shoulder girdle, head, neck and related conditions. The appliance includes a seat cushion surrounded on three sides by a three-sided vest having a back wall and a pair of forwardly extending sidewalls. The '264 patent teaches a medical appliance and is not an apparatus that can be used in conjunction with a stroller, carseat, or any place where a seated child fall asleep causing stress to their neck and impacting blood flow to the cerebral cortex.

U.S. Pat. No. 5,360,393 to Garth et al. discloses a dual adhesive strap which is designed to lay across and adhere to the patient's forehead and have each of its ends adhere to a spine board for securing a patient's head in a head immobilizer. The strap has a bottom side comprising a central region which comprises skin contact adhesive flanked by two regions which comprise a board contact adhesive. The '393 patent teaches a medical appliance and is not an apparatus that can be used in conjunction with a stroller, carseat, or any place where a seated child fall asleep. Furthermore, it is specifically designed to keep the wearers head firmly in place with little or no movement at all.

U.S. Pat. No. 6,209,959 to Meye discloses a headrest to be used in vehicles and provided with fastening means for a headband to be positioned around the head of a passenger above the eyes and ears. The fastening means comprise a ring suitable for the headband to be passed through. The fastening means comprise a band attached in the interior of the headrest, which extends through an opening in the upholstery, and the ring is fastened to the band at the exterior of the headrest. The '959 patent teaches a headrest for use with an adult seat and not as a retrofit which can be applied to a stroller, carseat, or any place where a seated child fall asleep. The lack of mobility associated with the use of this device can be harmful, especially for a young child, in the event of an accident.

U.S. Pat. No. 6,607,245 to Scher discloses a head restraint for supporting a user's head with respect to the headrest portion of a seat. The head restraint has a headband strap for placing over the head across the forehead of the user. An anchor band is secured around the headrest portion of the seat. A right-hand securement strap is affixed between the strap placed over the head of the user and the anchor band. Similarly, a left-hand strap is affixed between the strap placed over the head of the user and the anchor band. The '245 patent requires the user to wrap the bands entirely around the vehicle chair making it difficult to install in some seats and impossible in others. Moreover, the apparatus presents a safety risk and choking hazard in the unfortunate event should the disclosed band slip and end up around the wearer's neck.

U.S. Pat. No. 7,232,185 to Hartenstine et al. discloses a head rest for a car seat used to transport a child in an automobile which is positionally adjustable vertically along the seat back on which the head rest is mounted. A latching mechanism is actuated by a button at the top of the head rest and includes a releasable latch engagable with the channels slidably supporting the support rails of the head rest. A retainer clip is mounted at the top of the channels to prevent the head rest from being separated from the seat back once assembled thereon. The head rest includes a pair of laterally spaced wings that are pivotally connected to the rear support portion of the headrest to be positionally adjustable relative to the child's head through an angular displacement of approximately 45 degrees. The pivot mechanism is operable to lock the wings in the selected positions.

U.S. Pat. No. 7,740,318 to Funke, II et al. discloses an elastic, one-piece support band, a soft head pad which rests against an infant's head and two sets of fasteners. The support band passes through the head pad and is attached to a car seat with fasteners to support an infant's head in an upright position against the back of a car seat. The support band acts as a support system for a sleeping infant so that the infant's head does not roll around. This invention uses a lateral support to restrain the head and thereby unnecessarily restricts a significant amount of movement. This makes it uncomfortable and less capable of dissipating harmful forces resulting from a collision, sharp turn, sudden stop, or the like.

There exists a need for an apparatus that will secure a child's head and which can be attached as a retrofit to a stroller, carseat, high chair, or any place where a seated child falls asleep. An apparatus that will protect the head, spine, and nervous system of an occupant even while faced with the forces resultant from a vehicle being in motion and/or suddenly changing the direction of motion. There further exists a need for a child head and neck support apparatus that facilitates its operation with a wide variety of carseats as well as strollers and wheelchairs and high chairs. None of the aforementioned inventions suggest the novel features of the present invention. Applicants apparatus gives users a comfortable and easy to use means of ensuring their health by providing proper support to both their head and neck when they are unable to do so on their own.

SUMMARY

An object of the present invention is to ensure a child's head remains supported should they fall asleep while traveling in a carseat, stroller, or wheelchair. A head and neck support apparatus is provided that comprises a seat attachment portion and an portion which is worn by the seated individual. The worn portion comprises an elastic member that will, when worn, encircle the wearer's head. The rear of the worn portion will further comprise a first engagement member which will connect with a second engagement member removably connected to the seat where the child may foreseeably fall asleep.

In one embodiment, the aforementioned engagement members may be a hook-and-hoop fastener or similar means for releasable engagement. It is further envisioned that various other mating means may also be used. By way of example, and not limitation, such means include, but are not limited to, a snap fastener, buttons, magnets, or snap string ties as a mode for connecting the skull cap and seat to one another and holding the child's head up even while they are asleep.

In yet another embodiment, the worn portion of the apparatus may further comprise additional engagement members to better secure the child's head. By way of example, and not limitation, modern child seats typically come equipped with padding on the rear and both left and right sides of the child's head. In this embodiment of the invention, engagement members would be secured to the rear and at least one other side of the worn portion. The complementary engagement members would then be removably attached to the same side of the child seat so that a child's head is held in place from the rear and at least one other side thus reducing strain on the musculature of the neck.

In another embodiment, the present invention provides an apparatus to support the head and neck of a child who does not have the proper musculature to support it independently. The head and neck support apparatus comprises a skullcap comprising at least two removably attached absorption members. Each absorption member further comprises an installation means that allows the absorption member to be secured to any chair the child may be seated in. This absorbs some of the weight of the child's head in a position promoting oxygen delivery to the brain when forces may be acting on the child's head causing it to fall forward, to the side, or backwards.

The skullcap is preferably comprised of shock resistant elastic material that will allow some movement of the child's head while dissipating undesirable forces acting on the child The preferred location for attaching the absorption members is one directly above each temple of the child wearing the apparatus equally spaced around the perimeter of the skullcap. Attaching these members on the sides of child's head would substantially reduce the efficacy of the apparatus in minimizing the impact of external forces on the wearer's head and/or neck. The absorption members preferably pass behind the head of the wearer so that the installation means may be fasted to a support member behind the wearers head. By way of example and not limitation, such a support member may be the stalks for adjusting the height of a vehicle headrest or the stalks protruding from the back of a stroller or wheel chair. This type of vertical engagement is preferable over holding the head in place using support members located at the side of the child's head.

The absorption members may be releasably attached to the skullcap and support members. The means for releasable attachment may be a hook-and-loop fastener, or similar releasably attaching means. Non-limiting examples of other attachment means including zippers, buttons and corresponding button holes, and male and female snap buttons.

Such a child head and neck support apparatus comprises a number of benefits including but not limited to:
(i) blood flow to the child's brain remains uninterrupted when they fall asleep in an upright seating position;
(ii) the head of a child is allowed to sway slightly and change direction while they are asleep in an automobile, other vehicle seat, stroller or wheelchair while the neck is supported in a safe position;
(iii) the apparatus prevents that child from experiencing neck discomfort and allows the head of the child to remain in a safe position with minimal strain on the neck even while seated in an upright position;
(iv) such an apparatus is easy to install and maintain and is compact enough for efficient storage and transportation;
(v) can be secured as a retrofit in a automobile, other vehicle seat, stroller or wheelchair and most other places where a child's head and neck require additional support; and
(vi) keeps the child's head in a safe position away from the door of the motor vehicle they are a passenger in.

Other objectives, advantages, and novel features of the invention will become more apparent from the following detailed description when taken in conjunction with the accompanying drawings.

DESCRIPTION OF THE DRAWINGS

Figures

Figure 1:
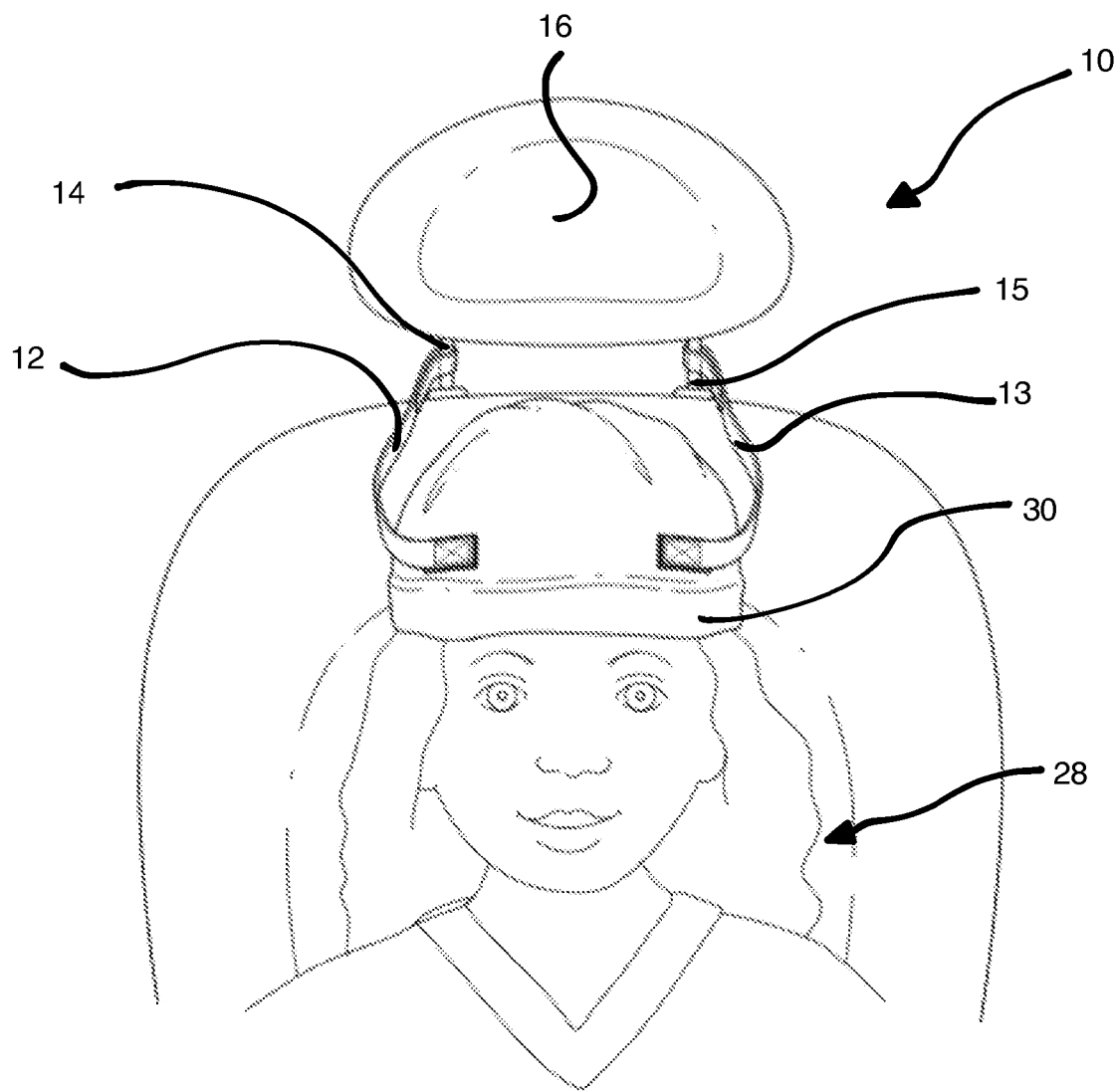
FIG. 1 is a front view of a head and neck support apparatus illustrated as worn by a young child in a car.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth." and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically or otherwise. Two or more electrical elements may be electrically coupled, but not mechanically or otherwise coupled; two or more mechanical elements may be mechanically coupled, but not electrically or otherwise coupled; two or more electrical elements may be mechanically coupled, but not electrically or otherwise coupled. Coupling (whether mechanical, electrical, or otherwise) may be for any length of time, e.g., permanent or semi-permanent or only for an instant.

DETAILED DESCRIPTION

Illustrative embodiments of the invention are described below. The showings are for purposes of illustrating preferred embodiments and not for purposes of limiting the same. The following explanation provides specific details for a thorough understanding of an enabling description for these embodiments. One skilled in the art will understand that the invention may be practiced without such details.

The head and next support apparatus of the present invention is illustrated in use in FIG. 1 and is indicated generally by reference character 10. The apparatus 10 has a pair of absorption straps 12 and 13 which are secured around the adjustment stalks 14 and 15 of a headrest 16. One end of each of absorption straps 12 and 13 may be looped around and secured to the respective stalks 14 and 15 using an engagement member such as a hook and loop fastener, buckle, button, or other similar means. The engagement members may be attached to the absorption straps 12 and 13 using a variety of means including, but not limited to, sewing glue and stitching.

As illustrated in FIG. 1, the child 28 is wearing a skullcap 30 placed around the top of her head. The skullcap 30 is sized to comfortably fit around a child's forehead. The skullcap 30 is preferably fabricated from a soft elastic material with at least some give. This material provides a soft cushioning effect and protects against sudden movements which may exert harmful forces on the child's head or neck.

Figure 2:
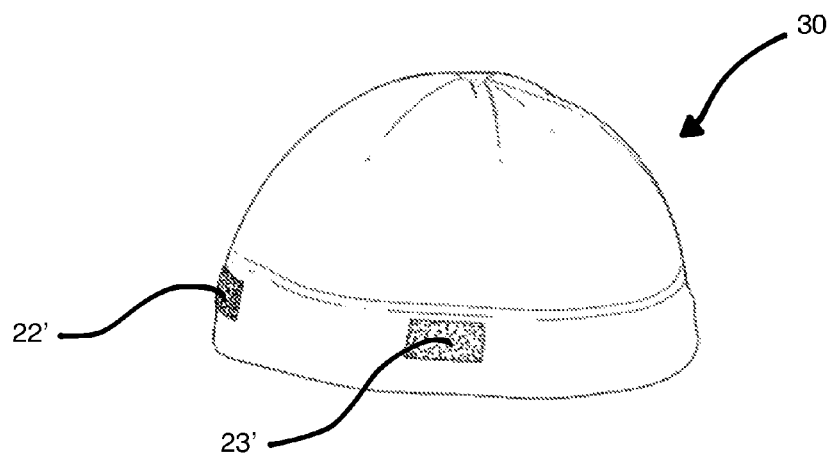
FIG. 2 is perspective view of the apparatus in FIG. 1 with the absorption members detached.
Figure 3:
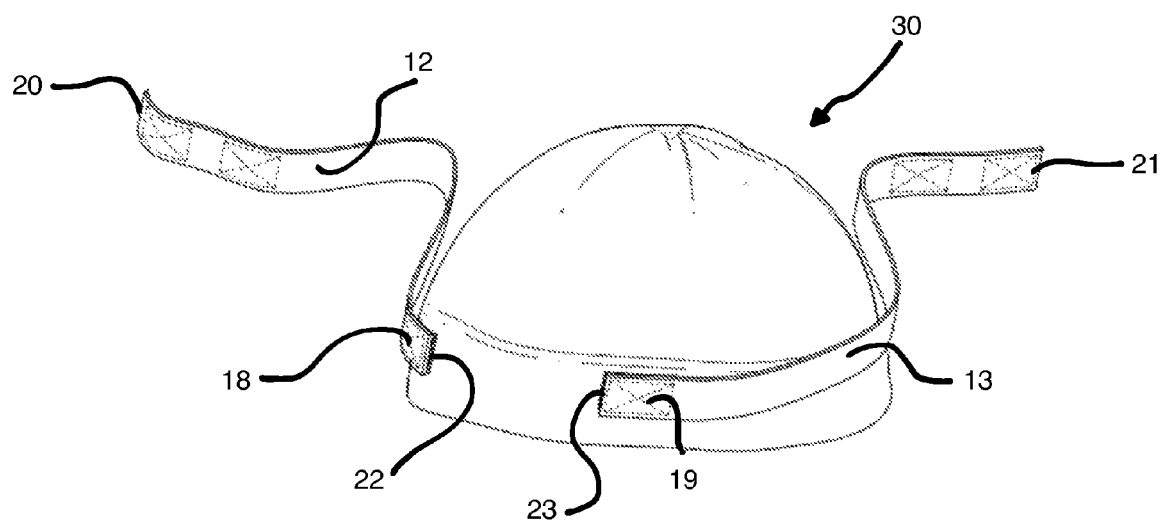
FIG. 3 is perspective view of the apparatus in FIG. 1 with the absorption members attached.
Figure 4:
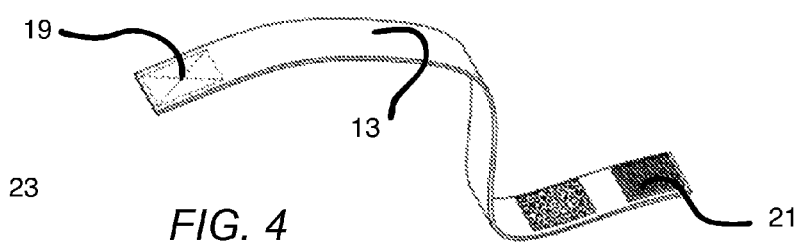
FIG. 4 is a perspective view on an absorption member comprising a hook and loop fastener.

The apparatus 10 is shown in exploded perspective view in FIGS. 2, 3, and 4. A righthand absorption straps 12 and a lefthand absorption straps 13 each have forward ends 18 and 19, respectively, and rearward ends 20 and 21, respectively. The forward ends 18 and 19 may be removably attached to the skullcap 30 as indicated by engagement members 22 and 23 on the forward ends and engagement member 22' and 23' on the skullcap 30. A variety of different means may be used for the engagement members including, but not limited to, hook and loop fasteners, buckles, buttons, or other similar means of releasably securing two separate members to one another. As mentioned, the engagement members may be attached to the absorption straps 12 and 13 using a variety of means including, but not limited to, sewing glue, stitching or other suitable process.

The absorption straps 12 and 13 are preferably fabricated from an elastic material with some give to provide multi-directional movement of the user's head and neck, thus minimizing discomfort while effectively keeping their head and neck in an upright position. Furthermore, the use of this material provides a cushioning effect which minimizes the impact of sudden movements that may exert harmful forces on the wearer's head or neck.

When worn, the forward ends 18 and 19 of the engagement members 22 and 23 on the absorption straps 12 and 13 and engagement members 22' and 23' on the skullcap 30 are positioned above the child's temples spaced equally apart from one another. The absorption members 12 and 13 travel behind the child's head rather than to the sides. This facilitates the process of securing the child's head and neck providing the maximum protection while minimizing any discomfort to the child. Accordingly, the child will have little or no trouble falling asleep while wearing the apparatus 10.

The amount of movement is adjustable to the user's discretion by the amount of tension applied when affixing the absorption straps 12 and 13.

Furthermore, absorption straps 12 and 13 need not be limited to installation on adjustment stalks 14 and 15 of a headrest 16. In one embodiment, the absorption straps 12 and 13 may be adapted for use with a stroller by securing the absorption straps 12 and 13 to parts of the stroller frame behind and to the left and right sides of the child's head respectively. Similarly, the absorption straps 12 and 13 may also be adapted for use by a child, or anyone with impaired neck muscles, seated in a wheelchair.

Figure 5:
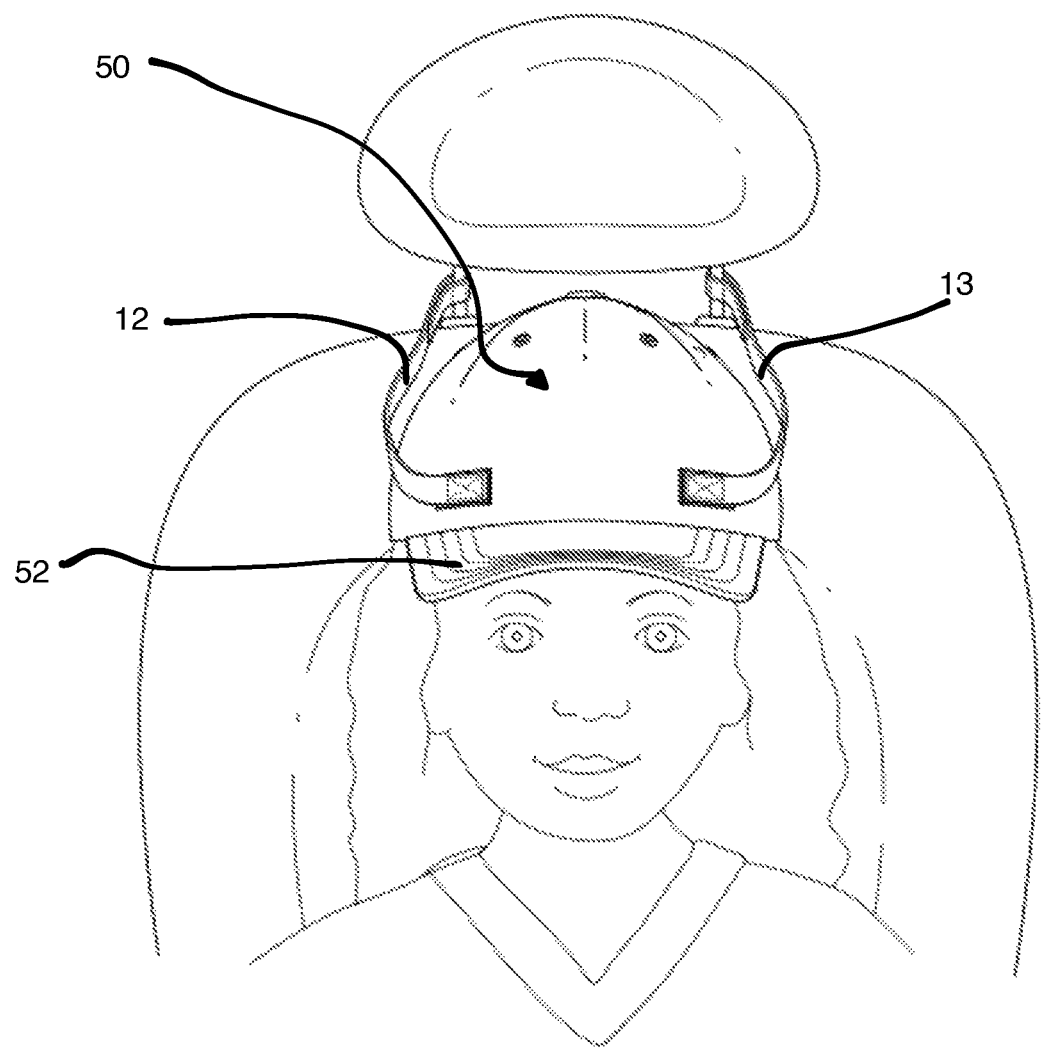
FIG. 5 is a front view of a head and neck support apparatus illustrated as worn by a young child in a car.

FIG. 5 is a front view of a head and neck support apparatus illustrated as worn by a young child in a car. In this embodiment, the skullcap 50 further comprises a brim 52 on the front of the skullcap 50. This embodiment has the added benefit of providing shade to the face of the wearer without interfering with the functionality of the apparatus 10.

Figure 6:
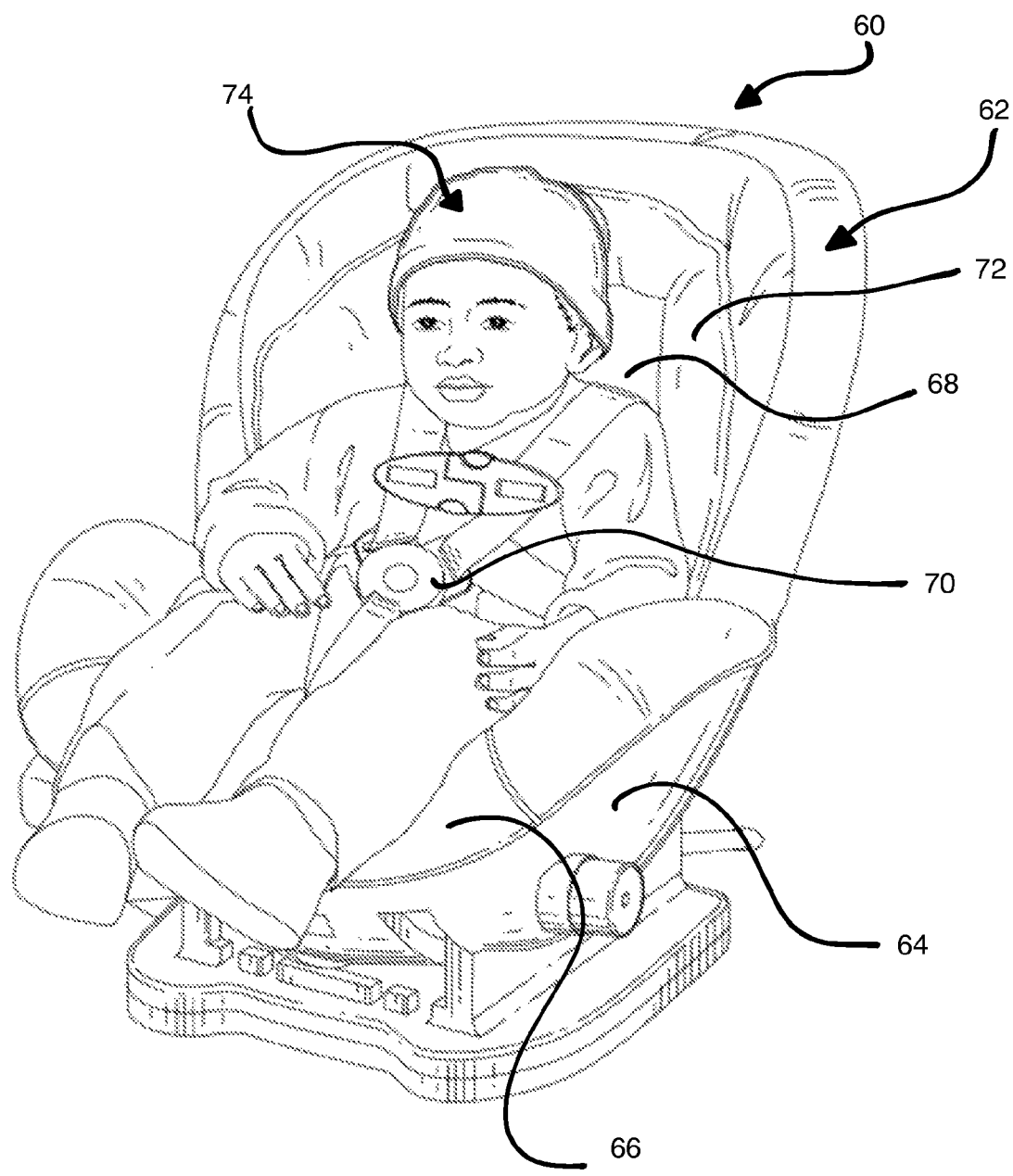
FIG. 6 is a perspective view of a head and neck support apparatus illustrated as worn by an infant in a car seat.
Figure 7:
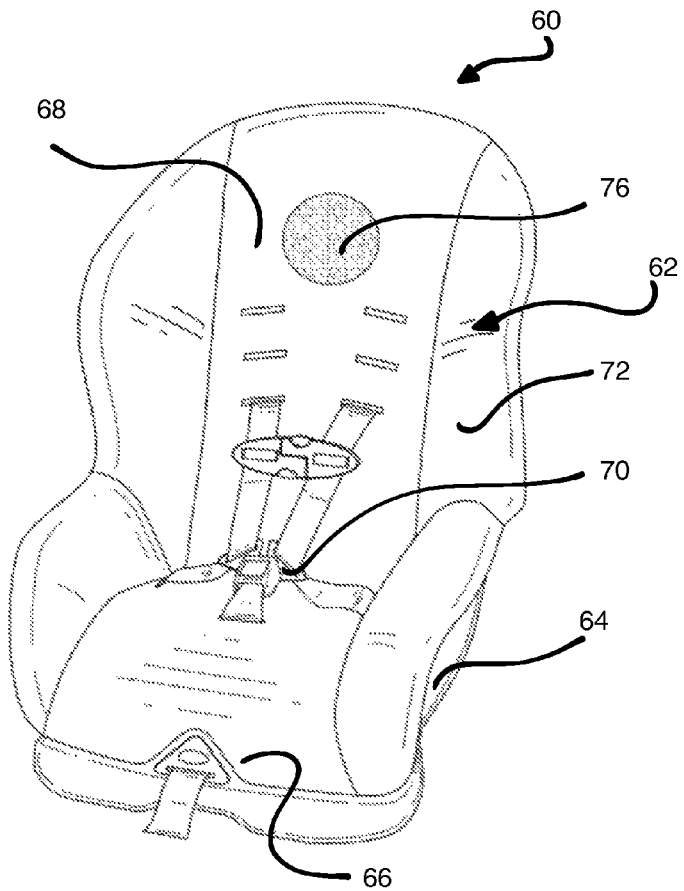
FIG. 7 is a perspective view of the carseat from FIG. 6 without the infant and the skullcap.
Figure 8:
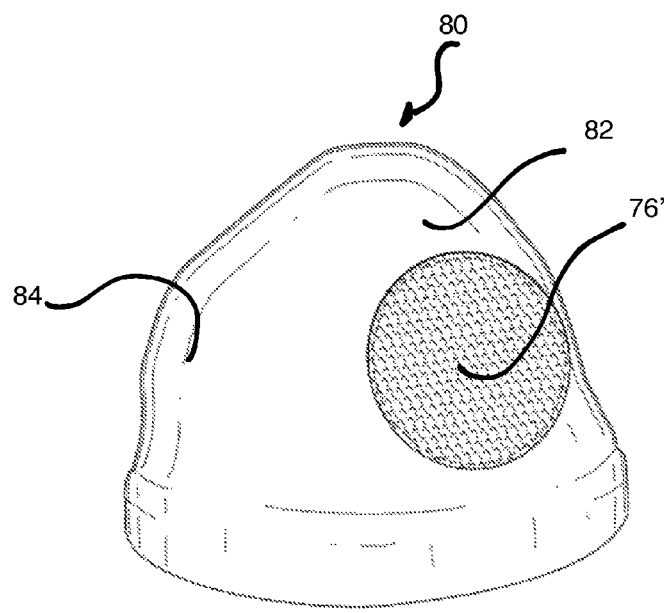
FIG. 8 is a perspective view of the skullcap from FIG. 6.

In another embodiment, referring now to FIGS. 6-8, the teachings of the present invention may be used to facilitate supporting the head and neck of a child seated in an infant carseat. The head and next support apparatus of this embodiment of present invention is illustrated in use in FIG. 6 and is indicated generally by reference character 60.

A cover 62 is removably attached onto an infant carseat assembly 64. In the preferred embodiment, the carseat assembly 64 comprises a seat 66 having backrest 68 and a safety harness 70. The seat may be adapted for use with a variety of different means for transporting a child including, but not limited to, a stroller. In one embodiment, attached to the cover 62 is a padded head bolster 72 that may be adjusted to reach the level of the child's head 74. These may be used by the child as a place to rest their head's while providing an added degree of protection in the event of a side-impact collision.

FIG. 7 Illustrates the carseat assembly 64 without the infant from FIG. 6. FIG. 8 illustrates the skullcap 80 being worn by the infant in FIG. 6. As seen in FIG. 7, the carseat cover 62 comprises an engagement member 76; in this example a hook and loop fastener. The engagement member 76 allows the skullcap 80 to be removably attached to the cover 62.

The cover 62 may be removably attached onto the skullcap 80 as indicated by engagement member 76 on the carseat cover 62 and a separate engagement member 76' on the backside of the skullcap 82. A variety of engagement members such as a hook and loop fastener, buckle, button, or other similar means of attaching the skullcap 80 to the cover 62 may be used. The engagement members may be attached to the cover 62 and skullcap 80 using a variety of means including, but not limited to, sewing glue, stitching or other suitable process.

In use, the engagement members 76 and 76' are aligned and engaged with one another after the skullcap is placed securely onto the child's head 74. In another embodiment, additional engagement members may be placed on the side head bolsters 72 with corresponding engagement members on the sides of the skullcap 84.

In all embodiments, the amount of movement experienced by the wearer's head and neck is reduced. A small amount of give in the skullcap minimizes discomfort felt by the wearer. Thus some of the weight from the wearer's head 74 is supported and the amount of strain on the wearer's neck and spine is reduced. Securing the head and neck in this position further ensures proper oxygenation to vital organs, particularly the cerebral cortex.

Although the invention has been described with reference to specific embodiments, it will be understood by those skilled in the art that various changes may be made without departing from the scope of the invention. Accordingly, the disclosure of embodiments is intended to be illustrative of the scope of the invention and is not intended to be limiting. It is intended that the scope of the invention shall be limited only to the extent required by the appended claims. To one of ordinary skill in the art, it will be readily apparent that the apparatus discussed herein may be implemented in a variety of embodiments, and that the foregoing discussion of certain of these embodiments does not necessarily represent a complete description of all possible embodiments. Rather, the detailed description of the drawings, and the drawings themselves, disclose at least one preferred embodiment, and may disclose alternative embodiments.

All elements claimed in any particular claim are essential to the embodiment claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents

CONCLUSIONS, RAMIFICATIONS, AND SCOPE

While a particular form of the invention has been illustrated and described, it will be apparent that various modifications can be made without departing from the spirit and scope of the invention. For example, the engagement members are illustrated as hook and loop fastener in some embodiments even though the inventor contemplates the possibility that the apparatus may be modified to suit a variety of means of engagement all the while comprising the properties of the invention. Accordingly, is not intended that the invention be limited, except as by the appended claims.

The teachings provided herein can be applied to other systems, not necessarily the system described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Particular terminology used when describing certain features or aspects of the invention should not be taken to imply that the terminology is being refined herein to be restricted to any specific characteristics, features, or aspects of the head and neck support apparatus with which that terminology is associated. In general, the terms used in the following claims should not be constructed to limit the head and neck support apparatus to the specific embodiments disclosed in the specification, unless the above description section explicitly define such terms. Accordingly, the actual scope encompasses not only the disclosed embodiments, but also all equivalent ways of practicing or implementing the disclosed apparatus. The above description of embodiments of the head and neck support apparatus is not intended to be exhaustive or limited to the precise form disclosed above or to a particular field of usage. While specific embodiments of, and examples for, the apparatus are described above for illustrative purposes, various equivalent modifications are possible which those skilled in the relevant art will recognize.

While certain aspects of the head and neck support apparatus are presented below in particular claim forms, the inventor contemplates the various aspects of the head and neck support apparatus in any number of claim forms. Accordingly, the inventor reserves the right to add additional claims after filing the application to pursue such additional claim forms for other aspects of the apparatus.

What is claimed is:

1. A head and neck support apparatus comprising:
   a seat comprising at least two support members, comprising a first support member and a second support member wherein said support members are adapted to be located behind the head of a user sitting in said seat;
   a first head absorption strap and a second head absorption strap, wherein said absorption straps each comprise a front end and a back end;
   said absorption straps each comprising at least one engagement member on said front end and at least two engagement members on said back end;
   said at least two engagement members on said back end of said first absorption strap are adapted to wrap around said first support member and releasably attach to one another;
   said at least two engagement members on said back end of said second absorption strap are adapted to wrap around said second support member and releasably attach to one another;
   a skullcap for placing over the head of a user extendable over a users forehead, wherein said skullcap comprises a first and second engagement member which are adapted to be positioned above the user's right and left temple respectively when said skullcap is worn by said user;
   said at least one engagement member on said front end of said first absorption strap being releasably attached to said skullcap first engagement member; and
   said at least one engagement member on said front end of said second absorption strap being releasably attached to said skullcap second engagement member.

2. The apparatus of claim 1 wherein said engagement members are hook and loop fasteners.

3. The apparatus of claim 1 wherein said absorption members are fabricated from elastic material.

4. The apparatus of claim 1 wherein said skullcap is fabricated from elastic material.

5. The apparatus of claim 1 wherein said seat is a stroller.

6. The apparatus of claim 1 wherein said seat is a wheelchair.

7. The apparatus of claim 1 wherein said seat is a seat in car.

* * * * *